US011033751B2

(12) United States Patent
Powell

(10) Patent No.: US 11,033,751 B2
(45) Date of Patent: Jun. 15, 2021

(54) PHOTO-TREATMENT DEVICE

(71) Applicant: Patrick Kenneth Powell, Farmington Hills, MI (US)

(72) Inventor: Patrick Kenneth Powell, Farmington Hills, MI (US)

(73) Assignee: ARBOR GRACE, INC., Detroit, MI (US)

(*) Notice: Subject to any disclaimer, the term of this patent is extended or adjusted under 35 U.S.C. 154(b) by 289 days.

(21) Appl. No.: 15/933,427

(22) Filed: Mar. 23, 2018

(65) Prior Publication Data
US 2018/0361171 A1    Dec. 20, 2018

Related U.S. Application Data

(60) Provisional application No. 62/475,261, filed on Mar. 23, 2017.

(51) Int. Cl.
*A61N 5/06* (2006.01)

(52) U.S. Cl.
CPC .......... *A61N 5/0616* (2013.01); *A61N 5/0614* (2013.01); *A61N 5/0621* (2013.01); *A61N 2005/063* (2013.01); *A61N 2005/0638* (2013.01); *A61N 2005/0657* (2013.01); *A61N 2005/0659* (2013.01); *A61N 2005/0661* (2013.01); *A61N 2005/0662* (2013.01); *A61N 2005/0666* (2013.01); *A61N 2005/0667* (2013.01)

(58) Field of Classification Search
CPC ...... A61N 5/06; A61N 5/0613; A61N 5/0614; A61N 5/0616; A61N 5/0618; A61N 5/062; A61N 5/0621; A61N 5/063; A61N 2005/063; A61N 2005/0632; A61N 2005/0635; A61N 2005/0636; A61N 2005/0637; A61N 2005/0638; A61N 2005/0643; A61N 2005/065; A61N 2005/0651; A61N 2005/0652; A61N 2005/0654; A61N 2005/0655; A61N 2005/0664; A61N 2005/0666; A61N 2005/0667; A61N 2005/067; A61N 5/0624; A61N 2005/0642
USPC ................................................ 607/88–91, 93
See application file for complete search history.

(56) References Cited

U.S. PATENT DOCUMENTS

| 3,877,437 A * | 4/1975 | Maitan ................. A61N 5/0621 607/91 |
| 6,045,575 A | 4/2000 | Rosen et al. |
| 6,464,715 B1 | 10/2002 | Gysens et al. |
| 6,596,016 B1 | 7/2003 | Vreman et al. |
| 6,811,563 B2 | 11/2004 | Savage, Jr. et al. |

(Continued)

FOREIGN PATENT DOCUMENTS

| DE | 3910238 | 3/1990 |
| FR | 2648036 | 12/1990 |
| WO | 2017004257 | 1/2017 |

*Primary Examiner* — Ahmed M Farah
(74) *Attorney, Agent, or Firm* — Carlson, Gaskey & Olds, P.C.

(57) ABSTRACT

A photo-treatment device includes a treatment region that has a front side at which source radiation is to be emitted and an opposite, back side. A plurality of light guides are located beside the treatment region. The light guides capture excess radiation peripheral to the treatment region and redirect the excess radiation toward the back side of the treatment region.

17 Claims, 11 Drawing Sheets

(56) References Cited

U.S. PATENT DOCUMENTS

| | | |
|---|---|---|
| 6,872,220 B2 | 3/2005 | Williams et al. |
| 7,147,653 B2 | 12/2006 | Williams et al. |
| 9,227,082 B2 | 1/2016 | McDaniel |
| 9,385,337 B2 | 7/2016 | Pan |
| 9,604,072 B2 | 3/2017 | Brezinski |
| 10,286,226 B2 | 5/2019 | Chakravarthy et al. |
| 2004/0039428 A1 | 2/2004 | Williams et al. |
| 2007/0032842 A1 | 2/2007 | Strong |
| 2007/0208397 A1 | 9/2007 | Gardner |
| 2007/0239232 A1* | 10/2007 | Kurtz .................. G02B 6/001 607/87 |
| 2008/0269844 A1 | 10/2008 | Logslett |
| 2009/0018622 A1 | 1/2009 | Asvadi et al. |
| 2010/0179469 A1 | 7/2010 | Hammond et al. |
| 2012/0253433 A1 | 10/2012 | Rosen et al. |
| 2012/0289885 A1* | 11/2012 | Cottrell ............... A61N 5/0616 604/20 |
| 2013/0226268 A1 | 8/2013 | Pan |
| 2014/0031906 A1 | 1/2014 | Brezinski |
| 2015/0217132 A1* | 8/2015 | Makkapati .......... A61N 5/0621 607/90 |
| 2016/0263396 A1 | 9/2016 | Chajravarthy et al. |
| 2017/0312542 A1 | 11/2017 | Palaniswamy et al. |
| 2018/0177434 A1 | 6/2018 | Kim et al. |
| 2018/0185664 A1* | 7/2018 | Powell .................. A61N 5/062 |
| 2018/0185665 A1 | 7/2018 | Osterhout et al. |
| 2018/0207446 A1 | 7/2018 | Jones |
| 2019/0099613 A1 | 4/2019 | Estes et al. |
| 2019/0099616 A1 | 4/2019 | Kavoori Sethumadhavan et al. |
| 2019/0224496 A1 | 7/2019 | Van Abeelen et al. |
| 2019/0232082 A1 | 8/2019 | Palaniswamy et al. |
| 2020/0038679 A1* | 2/2020 | Brezinski ................ A61F 7/08 |

\* cited by examiner

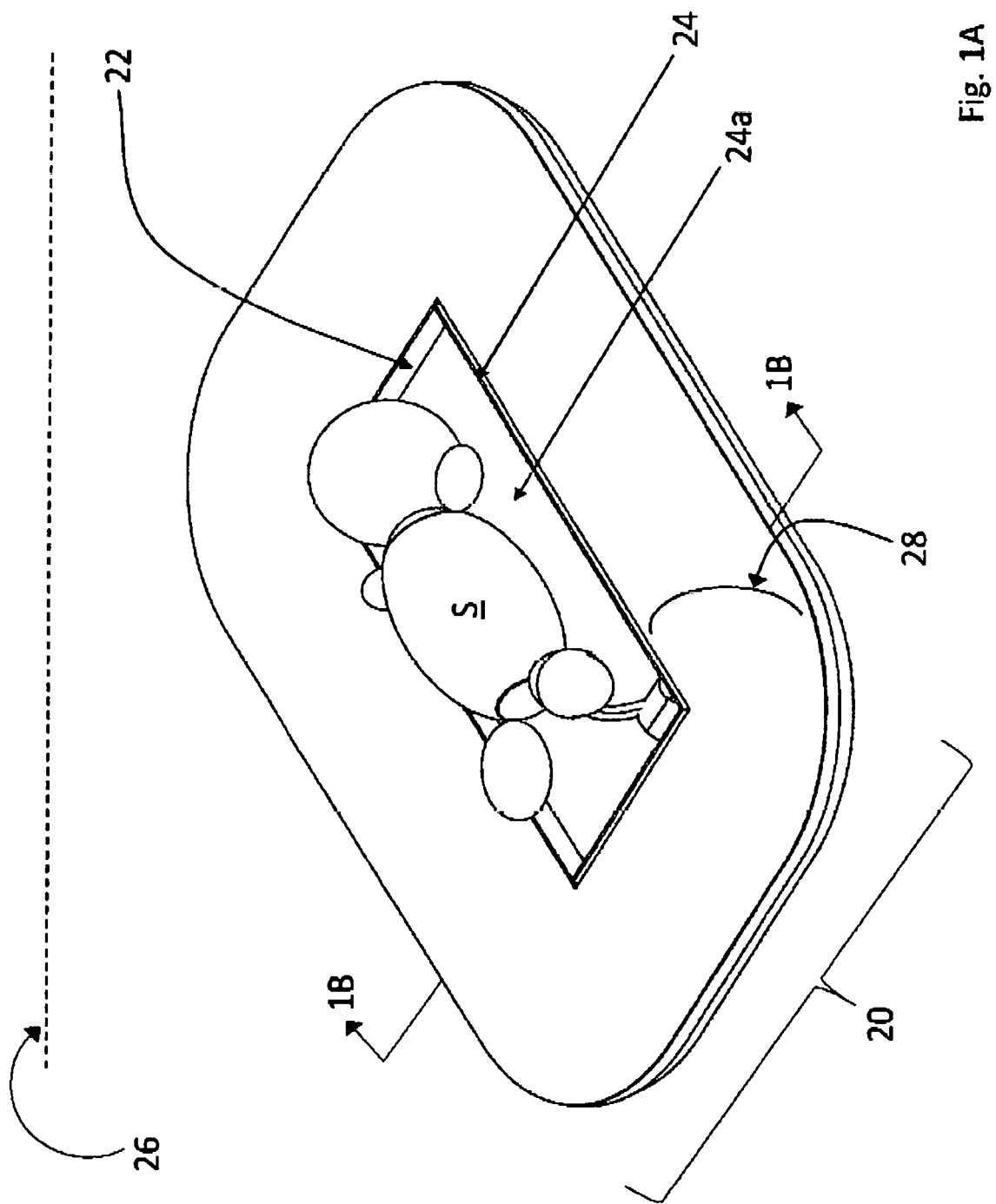

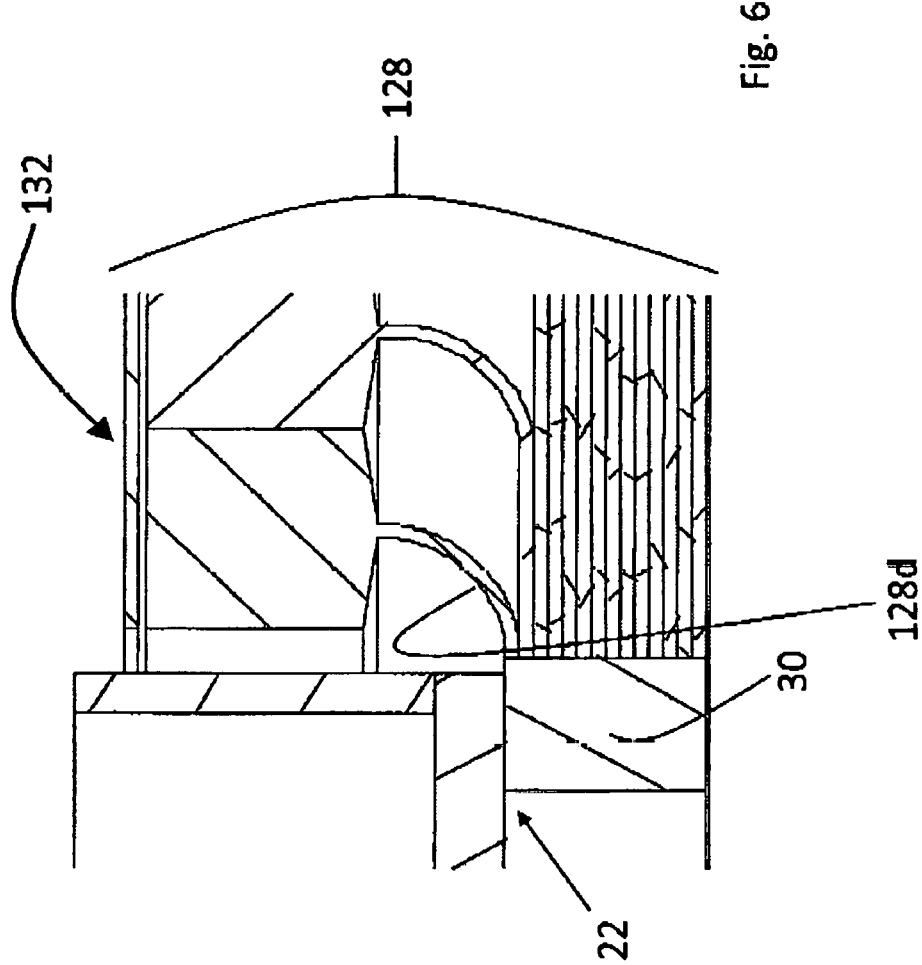

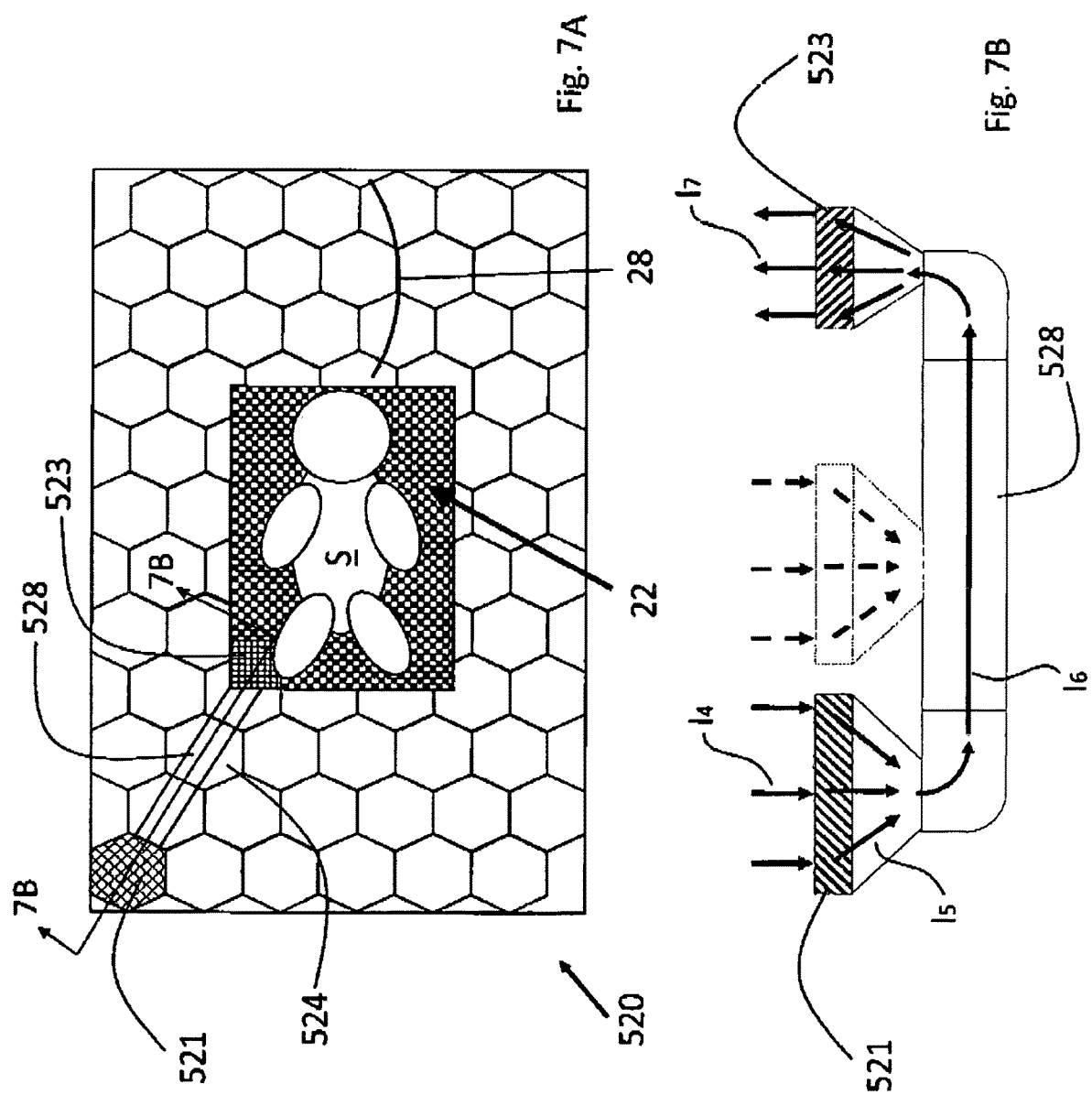

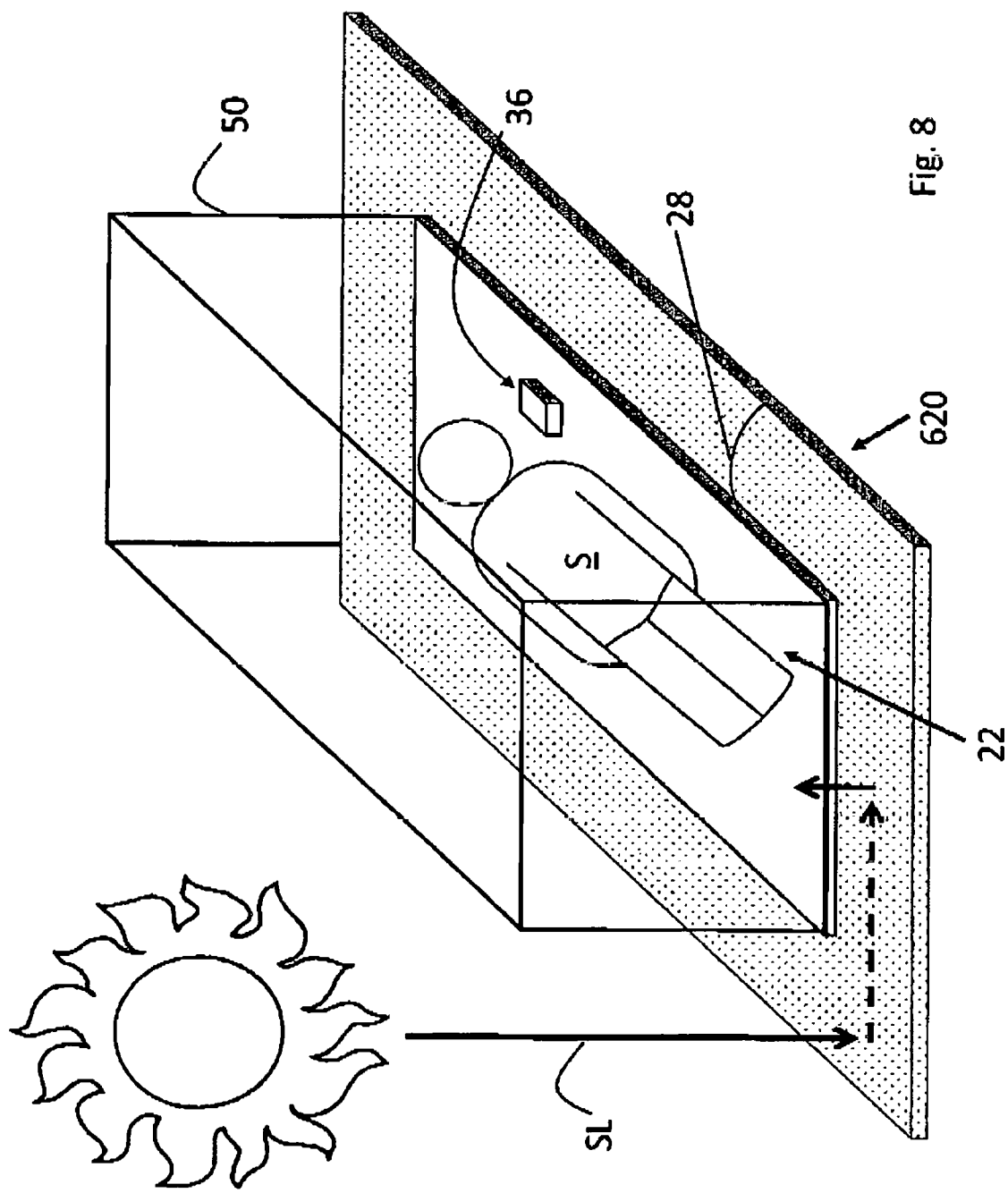

PHOTO-TREATMENT DEVICE

CROSS REFERENCE TO RELATED APPLICATION

This application claims priority to U.S. Provisional Application No. 62/475,261 filed Mar. 23, 2017.

BACKGROUND

Photo-treatment involves the emission of light or other radiation onto a subject. Such treatment is often used for medical purposes as a "photo-therapy." One example of photo-treatment involves using light to reduce bilirubin in infants. Light, most typically blue light, is directed at the infant. The light is absorbed through the infant's skin and causes a photo-reaction that chemically breaks down bilirubin. Most often, photo-therapy is provided by lights or a spotlight suspended above the subject to shine light directly onto the infant.

SUMMARY

A photo-treatment device according to an example of the present disclosure includes a treatment region that has a front side at which source radiation is to be emitted and an opposite, back side, and a plurality of light guides beside the treatment region. The light guides capture excess radiation peripheral to the treatment region and redirecting the excess radiation toward the back side of the treatment region.

In a further embodiment of any of the foregoing embodiments, the light guides are solid light pipes.

In a further embodiment of any of the foregoing embodiments, the light guides are nested with each other.

The photo-treatment device as recited in claim 1, further comprising one or more lenses focusing the excess radiation into the light guides.

In a further embodiment of any of the foregoing embodiments, the one or more lenses are position-adjustable relative to the light guides.

In a further embodiment of any of the foregoing embodiments, the one or more lenses are radiation-filtering with respect to one or more radiation wavelength bands.

In a further embodiment of any of the foregoing embodiments, each of the light guides circumscribes the treatment region.

In a further embodiment of any of the foregoing embodiments, the light guides are concentric.

In a further embodiment of any of the foregoing embodiments, the light guides are radiation-filtering with respect to one or more radiation wavelength bands.

In a further embodiment of any of the foregoing embodiments, the treatment region includes a non-opaque substrate.

In a further embodiment of any of the foregoing embodiments, the non-opaque substrate is radiation-filtering with respect to one or more radiation wavelength bands.

The photo-treatment device as recited in claim 10, further comprising a photovoltaic device arranged to receive the excess radiation through the non-opaque substrate.

In a further embodiment of any of the foregoing embodiments, the light guides are flexible.

The photo-treatment device as recited in claim 1, further comprising a reflective surface adjacent the back side of the treatment region.

The photo-treatment device as recited in claim 1, further comprising a radiation source operable to emit the radiation toward the treatment region.

In a further embodiment of any of the foregoing embodiments, the light guides terminate at a common surface.

In a further embodiment of any of the foregoing embodiments, each said light guide includes an enlarged collection head that narrows to a curved light pipe section, the curved light pipe section transitioning into a substantially flat horizontal light pipe section that terminates at the treatment region.

In a further embodiment of any of the foregoing embodiments, each said curved light pipe section of the respective light guides has a unique length.

In a further embodiment of any of the foregoing embodiments, the unique lengths increase with increasing distance from the treatment region.

A method of photo-treatment according to an example of the present disclosure includes causing radiation to be emitted from a radiation source onto a subject in a treatment region such that the radiation directly impinges on surfaces of the subject that are in a direct line of sight of the radiation source, and causing excess radiation that is peripheral to the treatment region and that does not directly impinge on the subject to be captured and redirected toward a back side of the treatment region such that the redirected excess radiation impinges on surfaces of the subject that are out of the direct line of sight of the radiation source. The subject thereby receives the radiation simultaneously on the surfaces that are in the direct line of sight of the radiation source and the surfaces that are out of the direct line of sight of the radiation source.

BRIEF DESCRIPTION OF THE DRAWINGS

The various features and advantages of the present disclosure will become apparent to those skilled in the art from the following detailed description. The drawings that accompany the detailed description can be briefly described as follows.

FIG. 1A illustrates an example photo-treatment device.

FIG. 6 illustrates another example photo-treatment device.

FIG. 7A illustrates another example photo-treatment device comprised of a grid of individual focus lenses, optical fibers, and dispersion lenses.

FIG. 7B illustrates a focus view of lens, transport, and dispersion onto the subject in FIG. 7A.

FIG. 8 illustrates another example photo-treatment device that can be used for tanning.

DETAILED DESCRIPTION

FIG. 1A schematically illustrates a photo-treatment device 20. The device 20 may be used for medical treatments, such as phototherapy to lower bilirubin levels in infants. It is to be understood, however, that the device 20 is not limited to medical treatments or bilirubin treatments and may also be used for non-medical treatments (e.g., tanning, photosynthesis) and other treatments using, for example, infrared radiation, ultraviolet radiation, visible light, sunlight, or filtered radiation. As will be appreciated from the examples herein, the photo-treatment device 20 serves to collect radiation that does not impinge directly on a subject and redirects that radiation to a portion of the subject that is otherwise shadowed from directly receiving the radiation.

Figure 1B:
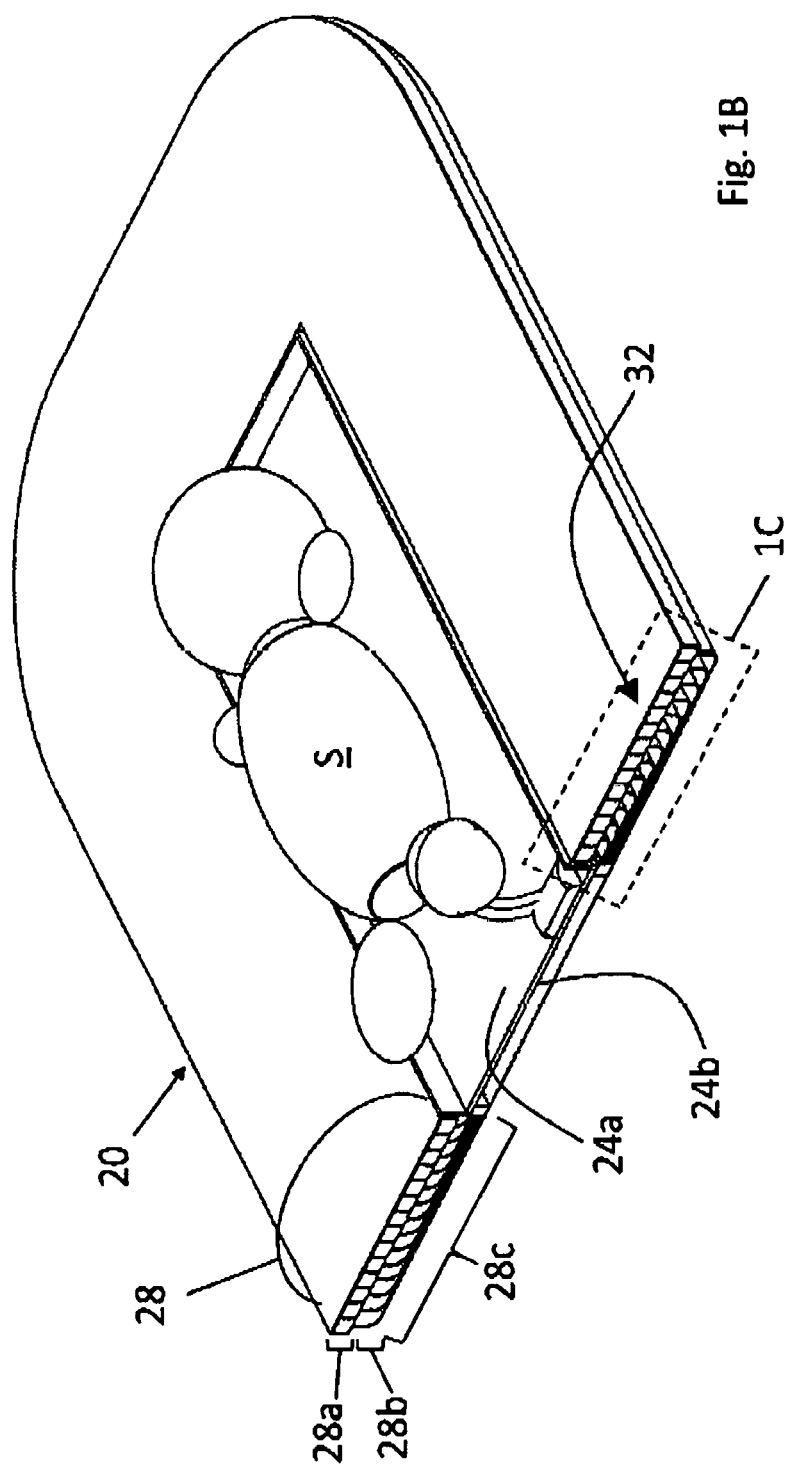
FIG. 1B illustrates a sectioned view of the photo-treatment device of FIG. 1A.
Figure 1C:
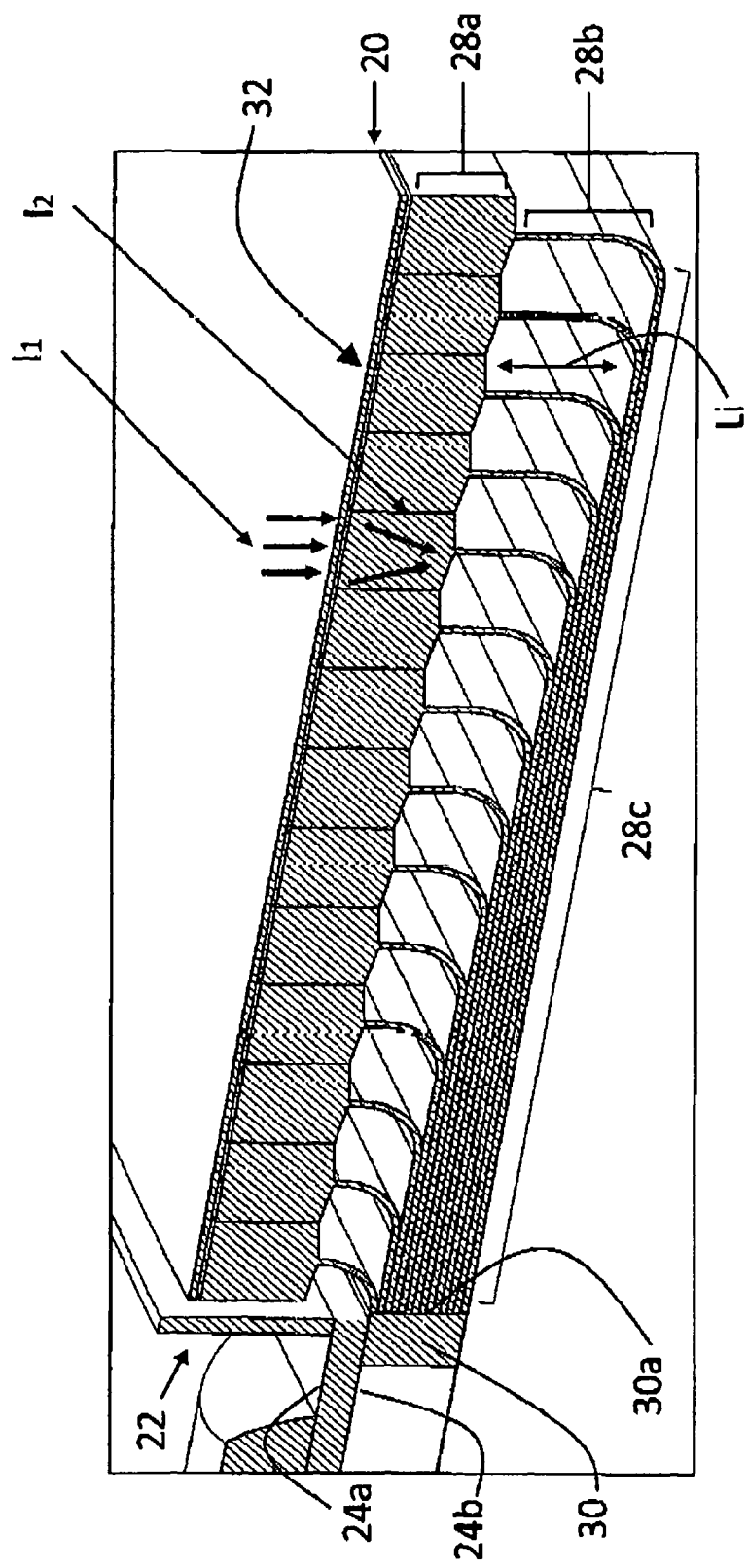
FIG. 1C illustrates a magnified view of a portion of the photo-treatment device of FIG. 1B.
Figure 1D:
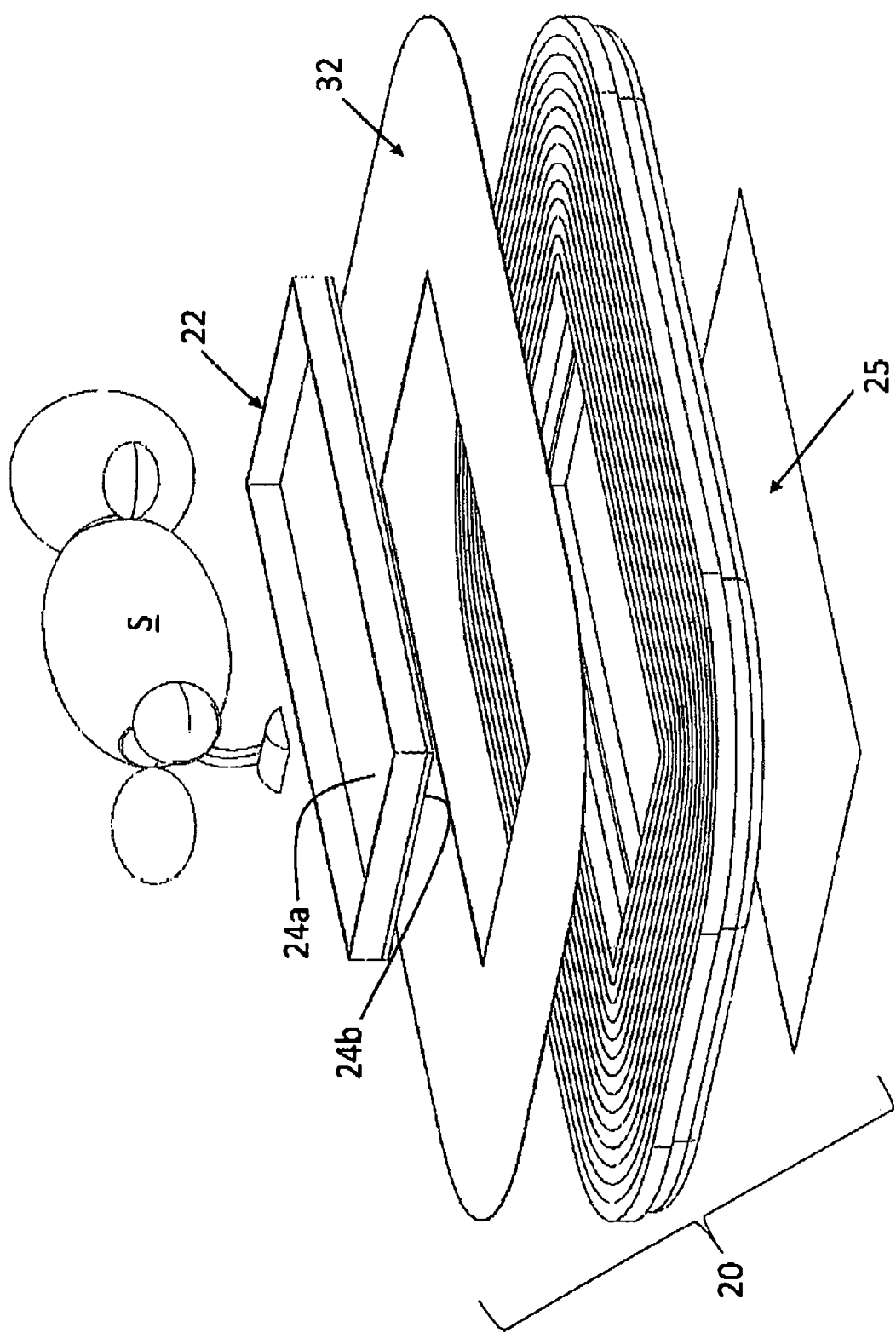
FIG. 1D illustrates an expanded view of the photo-treatment device of FIG. 1A.

Referring also to FIGS. 1B, 1C, and 1D, the device 20 includes a treatment region 22. Generally, the treatment region 22 is the space or region in which the subject of the treatment resides or is supported during treatment, such as an infant. Thus, for treatment of infants, the treatment region 22 may be sized accordingly. If the device 20 is instead designed for treatment of adults or other types of subjects, the treatment region 22 could be designed larger or smaller as appropriate for the subject.

The treatment region 22 may include a non-opaque substrate 24, which may be provided in the device 20 or provided separately from the device 20. The substrate 24 may be formed of a transparent or translucent material, such as polycarbonate, glass, clear or translucent fabrics, or the like, or wire or mesh materials that have openings that allow radiation transmission. In the case of wire or mesh, the wires may be solid/opaque, but the openings between woven wires permits transmission. The wire or mesh may thus be used to support the subject, as well as any absorbents, while thus permitting treatment. As used herein, terms such as opaque, translucent, transparent are made with reference to the type of radiation used. For instance, the substrate 24 may be transparent to visible light from a light/radiation source 26 above the device 20, although not necessarily transparent to other types of radiation.

The device 20 further includes light guides 28 beside the treatment region 22/substrate 24. The light guides 28 capture excess radiation peripheral to the treatment region 22 and redirect the excess radiation toward the back side 24b of the treatment region 22. A portion of the radiation emitted from the radiation source 26 impinges directly on surfaces of the subject, here shown at S, that are in the direct line of sight of the radiation source 26. This radiation impinges only on the side of the subject that is facing toward the radiation source 26. The area across which the radiation is projected is larger than the subject, and some of the radiation thus does not fall on the subject. In this regard, the light guides 28 capture excess radiation peripheral to the treatment region 22 and redirect the excess radiation to the backside 24b. This redirection to the backside 24b allows the excess radiation to impinge on the shadowed side of the subject that does not in the direct line of sight of the radiation source 26 and thus does not directly receive radiation from the radiation source 26, including pressure-points of the subject that are in contact with the substrate 24. The subject thus receives a higher percentage of the radiation from the radiation source 26, thereby increasing the dosage and enhancing the treatment.

To facilitate redirection of the radiation onto the shadowed side of the subject, the device may further include a reflective surface 25 adjacent the back side of the treatment region 22. For example, the reflective surface may be a mirror coating. The reflective surface 25 reflects redirected radiation toward the subject.

In the illustrated example, the light guides 28 are solid light pipes that are nested with each other. Like the substrate 24, the light guides 28 may be formed of a transparent or translucent material, such as polycarbonate or glass. The solid light pipes serve to redirect the excess radiation by internal reflection. Additionally or alternatively, the light guides 28 may include one or more optical fibers and/or hollow light pipes that serve to redirect the excess radiation by external reflection.

Each light guide 28 includes an enlarged collection head 28a that narrows to a curved light pipe section 28b. The tops of the collection heads 28a serve to collection the excess radiation. The curved light pipe section 28b transitions into a substantially flat horizontal light pipe section 28c that terminates at the treatment region, in this case a common surface 30a of a light diffuser 30. The curved light pipe sections 28b and the horizontal light pipe section 28c serve to direct the excess radiation to the treatment region 22. The light diffuser 30 facilitates uniform distribution of the radiation into the treatment region 22.

Each light guide 28 in this example circumscribes the treatment region 22, and the light guides 28 are concentric. The shape may be varied, to substantially match the projection of the radiation source 26, for example. As shown, the light guides 28 have a "racetrack" or ovular shape. Alternatively, the shape could be rectangular, circular, or polygonal.

In the nested arrangement, the first or outermost light guide 28 (relative to the treatment region 22) serves as the bottom nest. The next outermost light guide 28 fits within the outermost light guide 28 such that the enlarged collection heads 28a abut and form a substantially flush top surface. The collection heads 28a may be bonded together, or left separate to permit disassembly. The curved light pipe sections 28b are spaced apart, and the horizontal light pipe section 28c of the next light guide sits on the top surface of the horizontal light pipe section 28c of the outermost light guide 28. The remaining light guides 28 nest similarly, each nesting with the light guide 28 before it.

Although the light guides 28 are similarly shaped to each other, due to the stacked, nesting arrangement, the curved light pipe sections 28b have unique lengths. For instance, each curved light pipe section 28b defines a vertical length $L_i$ from its collection head 28a to its horizontal section 28c. As the light guides 28 are progressively stacked, shorter lengths $L_i$ are needed to bottom-out on the prior light guide 28 in the nest. In this regard, each length $L_i$ is unique, and the lengths $L_i$ increase with increasing distance from the treatment region 22 (or, inversely, decrease with decreasing distance from the treatment region 22). Similarly, the total curved lengths of the curved light pipe sections 28b are unique and the total curved lengths increase with increasing distance from the treatment region 22. When all of the light guides 28 are nested, each horizontal section 28c terminates at the common surface 30a of the light diffuser 30.

The device 20 may further include one or more lenses 32. The lens or lenses 32 are disposed on the top surface of the collection heads 28a of the light guides 28. As an example, although not limited, the lens or lenses 32 may be Fresnel lenses. The lens or lenses 32 focus the excess radiation into the light guides 28, as shown by incident excess radiation $I_1$ and focused excess radiation $I_2$ (FIG. 1D).

Figure 2:
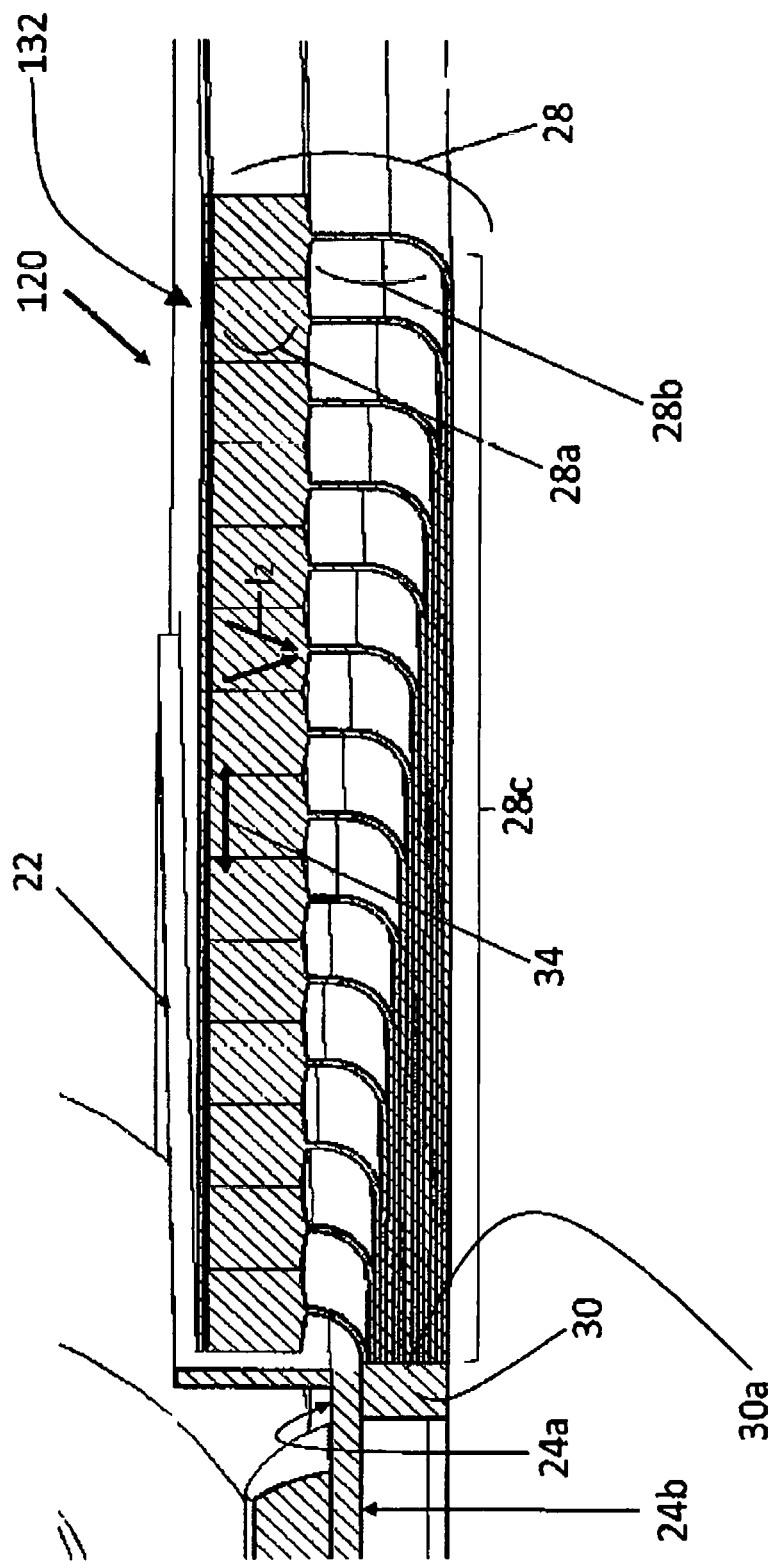
FIG. 2 illustrates another example photo-treatment device that has a position-adjustable lens.

As shown in FIG. 1C, the lens or lenses 32 are affixed with the light guides 28, by bonding or the like. FIG. 2 illustrates a modified example of a photo-treatment device 120. In this disclosure, like reference numerals designate like elements where appropriate and reference numerals with the addition of one-hundred or multiples thereof designate modified elements that are understood to incorporate the same features and benefits of the corresponding elements. The device 120 is the same as the device 20 but includes one or more position-adjustable lenses 132. As indicated at 34, the lens or lenses 132 are moveable relative to the light guides 28. This adjustability permits the lens or lenses 132 to be individually or collectively shifted in order to enhance the focused excess radiation $I_2$ into the light guides 28. For instance, the angle of the incident excess radiation may vary randomly or between different radiation sources. The lens or lenses 132 can thus be shifted in response to an instant angle of the incident excess radiation to optimize or improve the focus into the light guides 28. This shifting may be both lateral and rotational about the treatment region 22.

Figure 3:
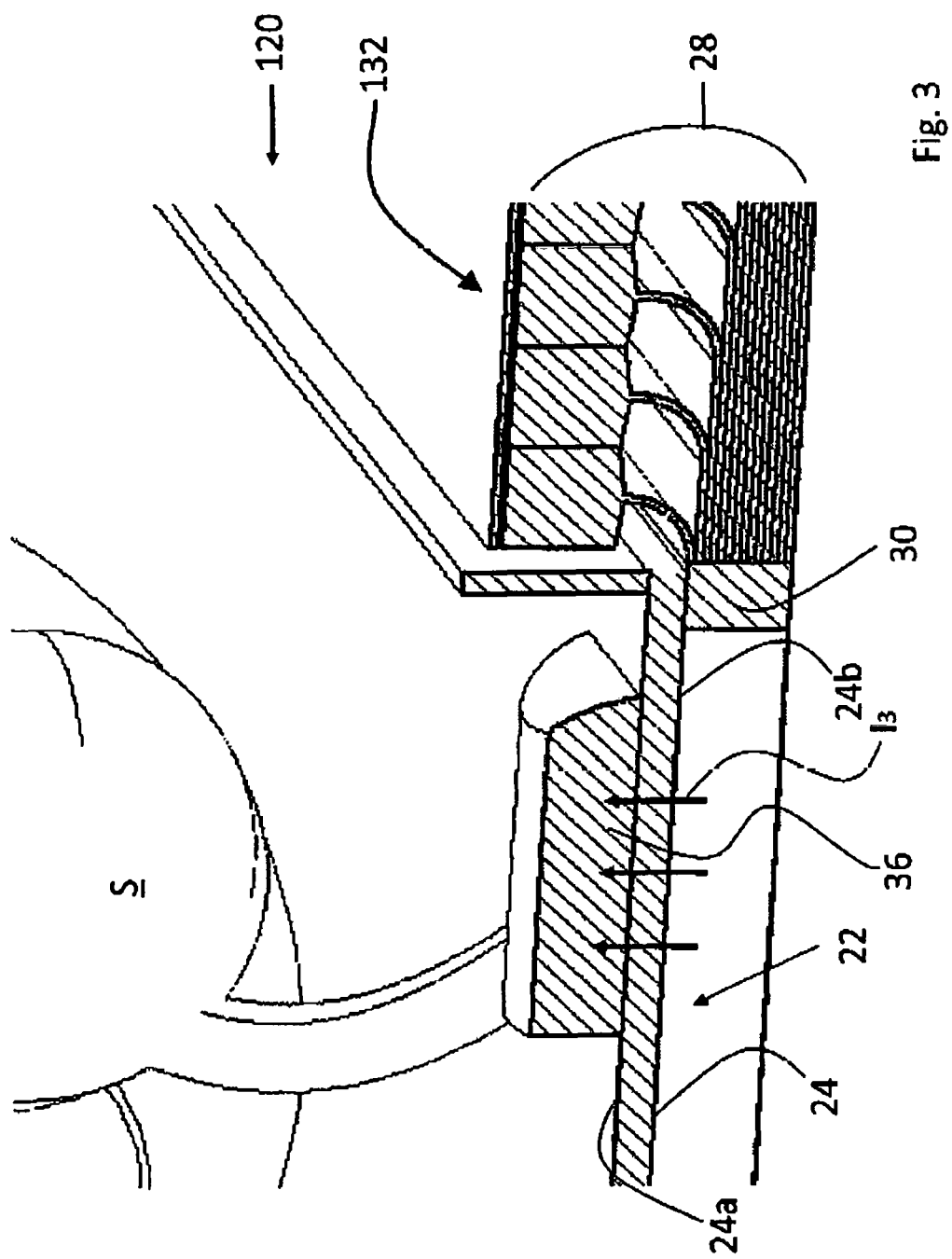
FIG. 3 illustrates another example photo-treatment device that includes a photovoltaic device.

FIG. 3 illustrates a further example in which the device 120 (or alternatively the device 20) includes a photovoltaic device 36. The photovoltaic device 36 may be free-floating (i.e., detached) in the treatment region 22, or alternatively attached or attachable to the substrate 24. The photovoltaic device 36 is arranged to receive the excess radiation through the non-opaque substrate, as shown at $I_3$. The photovoltaic device 36 may serve as a power source for a monitor or other device indicating the condition of the subject. In this regard, the photovoltaic device may also or additionally be secured to the subject.

Figure 4:
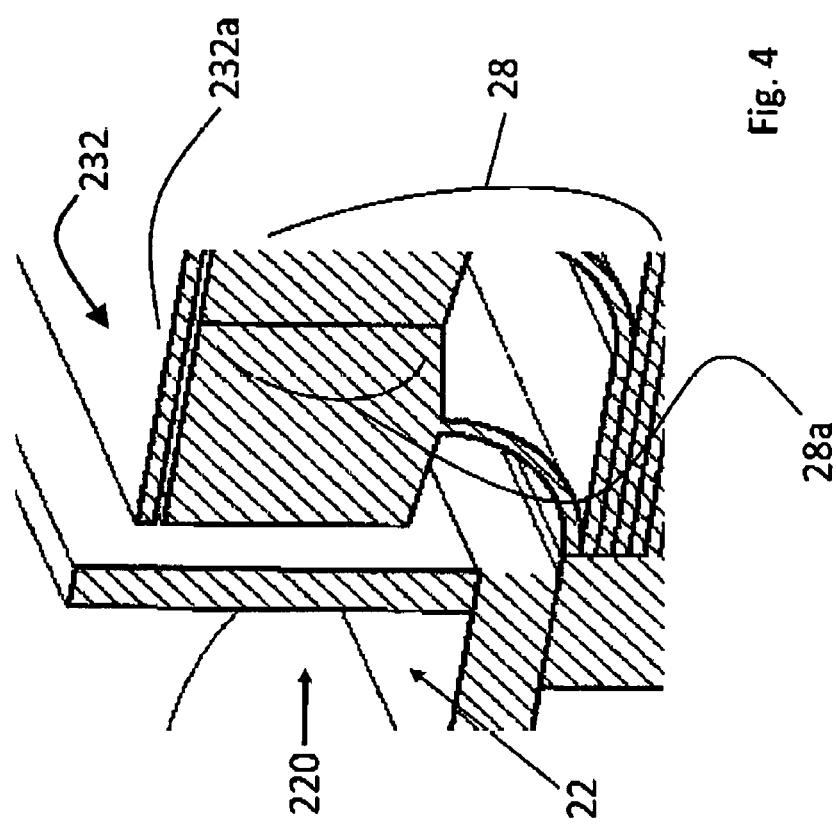
FIG. 4 illustrates another example photo-treatment device that has a radiation-filtering lens.

FIG. 4 illustrates another example of a photo-treatment device 220. The device 220 is the same as the device 120 except that the device 220 has a lens or lenses 232 that are radiation-filtering with respect to one or more radiation wavelength bands. For instance, the lens or lenses 232 include a film or additive 232a that modifies the light-transmitting behavior of the base material. As an example the coating or additive 232a is an organic dye or metal oxide pigment that absorbs and/or reflects specific bands of light (e.g., ultraviolet-A, ultraviolet-B, or ultraviolet-C). In this regard, the incident excess radiation is filtered such that only filtered excess radiation is transmitted to the treatment region 22.

Figure 5:
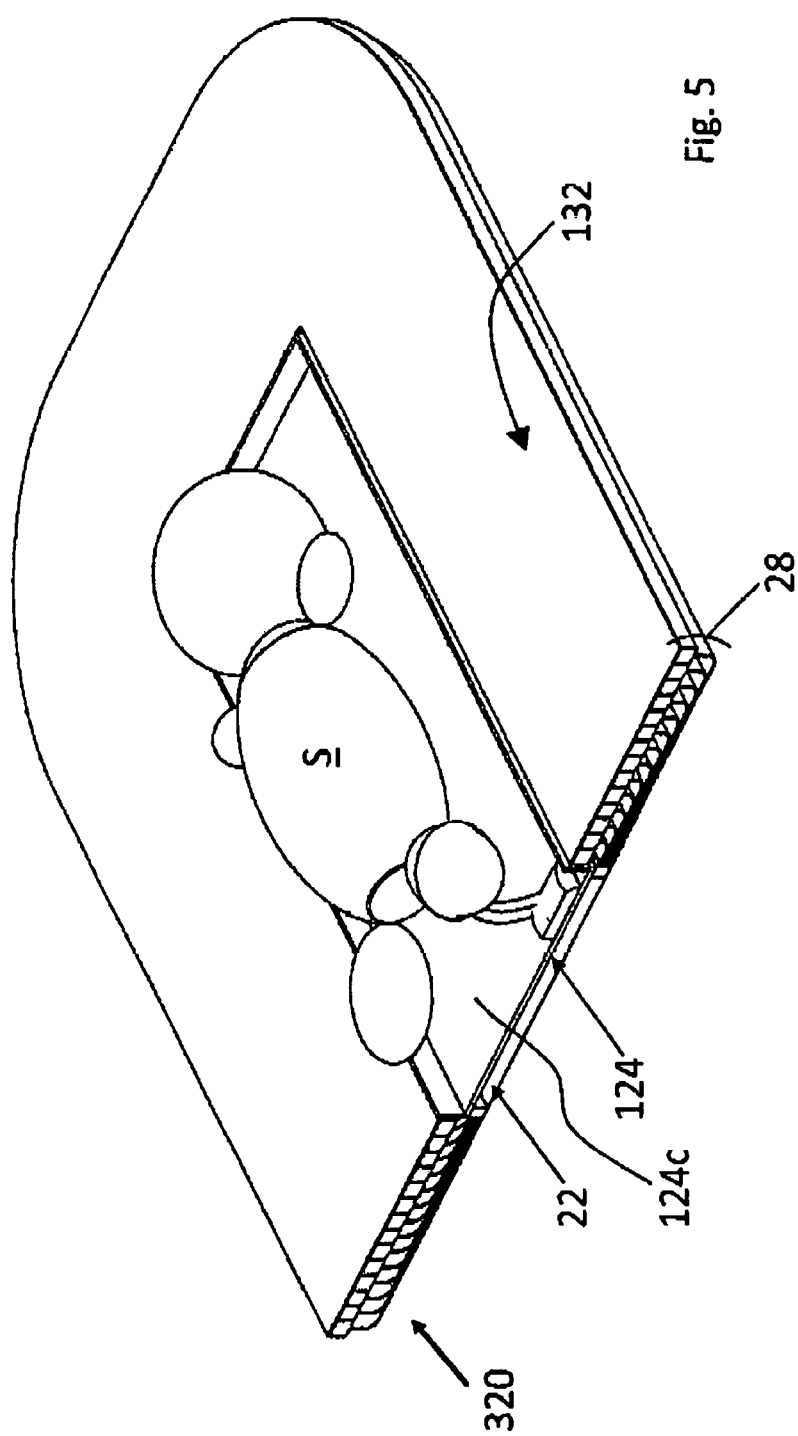
FIG. 5 illustrates another example photo-treatment device that has a radiation-filtering substrate.

FIG. 5 illustrates another example of a photo-treatment device 320. The device 320 is similar to the device 220 except that rather than the lens or lenses 232 that are radiation-filtering, the substrate 124 is radiation-filtering with respect to one or more radiation wavelength bands. For instance, the substrate 124 includes a film or additive 124c that modifies the light-transmitting behavior of the base material. As an example, the coating or additive 124c is an organic dye or metal oxide pigment that absorbs and/or reflects specific bands of light (e.g., ultraviolet-A, ultraviolet-B, or ultraviolet-C). In this regard, the incident excess radiation is filtered such that only filtered excess radiation is transmitted to the subject.

FIG. 6 illustrates another example of a photo-treatment device 420. The device 420 is similar to the device 220 except that rather than the lens or lenses 232 that are radiation-filtering, the light guides 128 are radiation-filtering with respect to one or more radiation wavelength bands. For instance, the light guides 128 include a film or additive 128d that modifies the light-transmitting behavior of the base material. As an example, the coating or additive 128d is an organic dye or metal oxide pigment that absorbs and/or reflects specific bands of light (e.g., ultraviolet-A, ultraviolet-B, or ultraviolet-C). In this regard, the incident excess radiation is filtered such that only filtered excess radiation is transmitted to the treatment region 22.

FIGS. 7A and 7B illustrate another example photo-treatment device 520. The device 520 includes a plurality of focus lenses 521, generally horizontal light guides 528, and dispersion lenses 523 placed in a grid array 524 with one or more lenses 521. The lenses 521 focus received radiation $I_4$, and focus the radiation (as shown at $I_5$) into the horizontal light pipes 528. The light guide 528 redirects the radiation $I_5$ to generally horizontal radiation $I_6$. The subject is in the treatment region 22, which includes the array of dispersion lenses 523. The lenses 523 receive the radiation $I_6$ and produce diffused radiation $I_7$, which impinges on the back side of the subject.

FIG. 8 illustrates another example photo-treatment device 620. In this example, the device 620 may be similar or the same as any of the prior devices, but larger in order to accommodate an adult subject. For instance, in one implementation, the device 620 may be used for tanning, in which the light guides 28 collect sunlight, as represented at SL, and redirect the sunlight to the shadowed underside of the subject, to provide a more balanced or uniform tanning system. As shown in phantom, an opaque or solid cover 50 may optionally be used to shield the subject from direct sunlight, thereby permitting tanning only of the underside. The device 620 may further include the photovoltaic device 36 within the enclosure.

Also disclosed is a method of photo-treatment. The method may include administration of treatment using, but not limited to, any of the devices disclosed herein. The method includes causing radiation to be emitted from a radiation source onto a subject in a treatment region such that the radiation directly impinges on surfaces of the subject that are in a direct line of sight of the radiation source and also causing excess radiation that is peripheral to the treatment region and that does not directly impinge on the subject to be captured and redirected toward a back side of the treatment region such that the redirected excess radiation impinges on surfaces of the subject that are out of the direct line of sight of the radiation source. The subject thereby receives the radiation simultaneously on the surfaces that are in the direct line of sight of the radiation source and the surfaces that are out of the direct line of sight of the radiation source.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from this disclosure. The scope of legal protection given to this disclosure can only be determined by studying the following claims.

What is claimed is:

1. A photo-treatment device comprising:
   a treatment region having a front side at which source radiation is to be emitted and an opposite, back side; and
   a plurality of light guides beside the treatment region, the light guides capturing excess radiation peripheral to the treatment region and redirecting the excess radiation toward the back side of the treatment region, each said light guide including an enlarged collection head that narrows to a curved light pipe section, the curved light pipe section transitioning into a substantially flat horizontal light pipe section that is substantially parallel to the back side and that terminates at the treatment region.

2. The photo-treatment device as recited in claim 1, wherein the light guides are solid light pipes.

3. The photo-treatment device as recited in claim 1, wherein the light guides are nested with each other.

4. The photo-treatment device as recited in claim 1, further comprising one or more lenses focusing the excess radiation into the light guides.

5. The photo-treatment device as recited in claim 4, wherein the one or more lenses are position-adjustable relative to the light guides.

6. The photo-treatment device as recited in claim 4, wherein the one or more lenses are radiation-filtering with respect to one or more radiation wavelength bands.

7. The photo-treatment device as recited in claim 1, wherein each of the light guides circumscribes the treatment region.

8. The photo-treatment device as recited in claim 7, wherein the light guides are concentric.

9. The photo-treatment device as recited in claim 1, wherein the light guides are radiation-filtering with respect to one or more radiation wavelength bands.

10. The photo-treatment device as recited in claim 1, wherein the treatment region includes a non-opaque substrate.

11. The photo-treatment device as recited in claim 10, wherein the non-opaque substrate is radiation-filtering with respect to one or more radiation wavelength bands.

12. The photo-treatment device as recited in claim 10, further comprising a photovoltaic device arranged to receive the excess radiation through the non-opaque substrate.

13. The photo-treatment device as recited in claim 1, wherein the light guides are flexible.

14. The photo-treatment device as recited in claim 1, further comprising a reflective surface adjacent the back side of the treatment region.

15. The photo-treatment device as recited in claim 1, further comprising a radiation source operable to emit the radiation toward the treatment region.

16. The photo-treatment devices recited in claim 1, wherein each said curved light pipe section of the respective light guides has a unique length.

17. The photo-treatment devices recited in claim 16, wherein the unique lengths increase with increasing distance from the treatment region.

* * * * *